United States Patent [19]

Scolastico et al.

[11] Patent Number: 4,950,776

[45] Date of Patent: Aug. 21, 1990

[54] PHARMACEUTICAL COMPOSITIONS FOR THE THERAPY OF INVOLUTIVE CEREBRAL SYNDROMES

[75] Inventors: Carlo Scolastico; Camillo M. Palazzi, both of Codogno, Italy

[73] Assignee: S. Team S.R.L. Corso Lodi, 47, Milan, Italy

[21] Appl. No.: 112,000

[22] PCT Filed: Feb. 12, 1987

[86] PCT No.: PCT/EP87/00068

§ 371 Date: Oct. 8, 1987

§ 102(e) Date: Oct. 8, 1987

[87] PCT Pub. No.: WO87/05024

PCT Pub. Date: Aug. 27, 1987

[51] Int. Cl.$^5$ .................. C07F 9/10; A61K 31/685
[52] U.S. Cl. ........................................ 558/169; 514/77
[58] Field of Search ........................... 514/77; 558/169

[56] References Cited

U.S. PATENT DOCUMENTS

| | | | |
|---|---|---|---|
| 4,595,680 | 6/1986 | della Valle et al. | 514/77 |
| 4,624,852 | 11/1986 | Wurlman | 514/77 |
| 4,624,946 | 11/1986 | Scolastics et al. | 514/77 |
| 4,775,758 | 10/1988 | Nojima et al. | 558/169 |

FOREIGN PATENT DOCUMENTS 3212387A 10/1983 Fed. Rep. of Germany ........ 514/77
2057872 9/1979 United Kingdom .

*Primary Examiner*—Jacqueline V. Howard

[57] ABSTRACT

Pharmaceutical compositions active on cerebral metabolism and on neuronal transmission containing as the active principle glycerophosphoryl-O-serine.

19 Claims, No Drawings

PHARMACEUTICAL COMPOSITIONS FOR THE THERAPY OF INVOLUTIVE CEREBRAL SYNDROMES

This invention relates to pharmaceutical compositions suitable for the therapy of involutive cerebral syndromes, containing as the active principle glycerophosphoryl-O-serine (herinafter indicated also as GPS) or its salts with alkali or alkali earth metals.

Pharmaceutical compositions containing as the active principle phosphatidylserine (PS), suitable for the therapy of psycho-organic syndromes due to an involutive origin, or to cerebrovascular deficiency, are known and used.

Phosphatidylserine (PS) is generally extracted from mammals brain in admixture with phosphatidylethanolamine ("cephalinic fraction") and subsequently purified. From a chemical point of view, PS is the double-acylated product with fatty, mainly unsaturated acids at the hydroxy groups of the glycerine residue of glycerophosphonyl-O-serine; but due to the presence of the unsaturated fatty acid, PS turns out to be unstable since it easily undergoes peroxydation. For example, standard α-phosphatidyl-L-serine decomposes in fact at room temperature, in an amount of 0.5% per day (Sigma Catalogue—1986 Ed., p. 971).

As a result of this fact complex stabilization techniques are used in order to minimize instability in the extractive phase, during the purification and the finished product.

From a biochemical point of view, phosphatidylserine is known to stimulate ACh release from the cerebral cortex in the anaesthetized rat. The stimulation may be inhibited by dopaminergic antagonists and by lesions in the septum (J. Neurochem. 32, 529, 533).

These data suggest that PS indirectly acts stimulating a dopaminergic system which, in its turn, increases ACh output from the cholinergic nervous terminations, which cholinergic fibers stimulated by PS derive from or go through the septum (Cholinergic Mechanism: Phylogenetic Aspects, Central and Peripheral Synapses, Clinical Significance—Ed. by E. Pepen Plenum Publishing Co., N.Y. 1981, 685).

It has also been shown that PS prevents scopolamine induced disruption of spontaneous alternations in newborn rats (in: Aging of the brain and dementia—Ed. by Amaducci—Raven Press N.Y. 1980, 271).

By evaluating the inhibition of the scopolamine electrocorticographic effects in the rat or in rabbit by PS, a further confirmation of the influence of the same on the cholinergic cortical mechanisms, is achieved (phospholipids in the Nervous System Vol. 1—Ed. by L. Horrocks—Raven Press N.Y. 1982, 165).

Haloperidol antagonizes ACh increase in the striatum induced by PS; the PS in its turn decreases the ACh spontaneous output from striatum slices. These data, as a whole, prove that PS is able to activate dopaminergic receptors in the caudatum (Phospholipids in Nervous System Vol. 1, Ed. by L. Horrocks, Raven Press N.Y. 1982, 165).

This gives value to the hypotheses that stimulation of ACh output from the cerebral cortex may be mediated by the activation of subcortical dopaminergic mechanisms.

It has been moreover shown that low doses of PS increase noradrenaline turnover, activate thyrosine-hydroxylase and accumulate c-AMP mainly in the hypothalamus (Life SCI. 23, 1093, 1978).

A direct cerebral effect of PS is supported by experiments in which, by injecting PS both intracerebroventricularly and intravenously, there are produced the same stimulating effects as evidenced on decreased learning ability in old rats (J. Lipid Res. 21, 1053, 1980).

However, this is not sufficient to confirm whether PS is active per se, or after metabolic conversion.

On the other hand, the metabolic fate of the exogenous PS administered orally and by i.v. involves the conversion thereof by monodeacylation into lyso-PS (Acta Physiol. Scand. 34, 147, 1954; Phospholipids in Nervous System vol. 1, Metabolism Ed. by L. Horrocks, Raven Press N.Y. 1981, 173).

By evaluating the kinetics by means of $[U^{14}-C]$ PS, it is evidenced that the amount of lyso-PS gradually increases in the blood and decreases in the liver and brain (J. Neurochem. 33, 1061, 1979). This reflects the reacylation rate of lyso-PS occurring in the liver and brain. On the contrary, however, formation of lyso-PS may occur in the blood, mediated by a phospholipase $A_2$ (Brit. J. Pharmacol. 66, 167, 1979; Biochem. 18, 780, 1969).

It is interesting to note that lyso-PS is endowed with pharmacological activity eight times higher than PS (Brit. J. Pharmacol. 66, 167, 1979).

It has now been surprisingly found that glycerophosphoryl-O-serine (GPS) is endowed with a pharmacological activity which is equal or higher than that of phosphatidylserine and with a far longer stability. This results in obvious advantages in the preparation and use of pharmaceutical formulations, which may be preserved for a long time without an appreciable decrease of activity.

It has been moreover found that GPS salts with alkali and alkali-earth metals, particularly the di-sodium, di-potassium, mono-calcium and mono-magnesium salts, up-to-now not known, are particularly suited for use in said formulations. This is particularly true for the mono-calcium salt. The advantages connected with the use of these salts, and especially of the monocalcium salt, in the substitution of glycerophosphoryl-O-serine in form of free acid are constituted by ease of purification of the same salts at the end of the preparation process; by their lower hydroscopicity (optimal for the calcium salt); and by their adaptability to use in pharmaceutical composition, due to the fact that the salts themselves, poorly hygroscopic, may be preserved for a long period without appreciable alteration.

A further object of the invention is to provide GPS salts with alkali or alkali-earth metals, particularly the monocalcium salt. This further object of the invention is achieved by a process for the preparation of GPS salts with alkali and/or alkali-earth metals, which comprises reacting GPS, in an aqueous medium, with a stoichiometric amount of a hydroxide, a carbonate or an acid carbonate of an alkali or alkali-earth metal, so that from the resulting aqueous solution the obtained salt can be isolated by evaporation or freeze-drying.

The following examples are meant to illustrate the process according to the invention, without limiting in any way the scope thereof.

EXAMPLE 1

2.27 ml (18.24 mol) of D-α,β-isopropylidene glycerol ((S)-2,2-dimethyl-1,3-dioxolane-4-methanol), dissolved in 18.2 ml of 2,6-lutidine, are added to the solution of 1.78 ml (19.15 mmol.) of POCl$_3$ in 19 ml of 2,6-lutidine, cooled to −6° C., under nitrogen and during 20′, not allowing the temperature to raise above 0° C.

After 30 minutes at −6° C., 6 g (18.24 mmol.) of N-benzyloxycarbonyl-L-serine benzylester dissolved in 36.5 ml of 2,6-lutidine, are added in 20′. The mixture is stirred at −6° C. for 2 hours, then a NaHCO$_3$ aqueous solution is added up to pH 6.5, evaporating thereafter the solution under vacuum (0.1 mm Hg) at a temperature of 35°–40° C., keeping the pH at 6.5. The residue is treated with 50 ml of water. The lutidinium salt is extracted with 4×30 ml of CHCl$_3$, the collected chloroform extracts are dried and evaporated under vacuum.

The residue is treated with 10 ml of a 95:5 CHCl$_3$CH$_3$OH mixture (by volume), containing 2% of triethylamine and applied on a Kieselgel ® 60 column, 230–400 mesh (Merck), eluting with the same mixture. The fractions containing the pure product are collected and evaporated under reduced pressure.

The residue (about 7 g) is taken up with 80 ml of CH$_3$OH/H$_2$O (1:1 by volume) and hydrogenated at room temperature and pressure on 1.16 g of charcoal containing 10% of palladium. When the H$_2$ absorption is over, the mixture is filtered and the catalyst is washed with 2>20 ml of CH$_3$OH/H$_2$O 1/1. The filtrate is evaporated under reduced pressure.

The residue is taken up with 10 ml of water; the solution is applied on a column having a diameter of 3 cm containing about 55 ml of wet Amberlite IR 120 (H$^+$) ® resin, equal to about 10 eq/mole. After elution with water, the eluate is evaporated under vacuum; the remaining traces of H$_2$O are eliminated under high vacuum in the presence of P$_2$O$_5$.

2.8 g of D-glycerophosphoryl-O-L-serine, having formula:

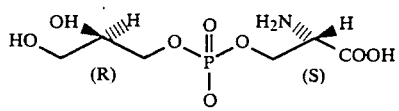

in a vetrous, highly hygroscopic state, are obtained.

From the aqueous solution of said residue, by addition of the stoichiometric amounts of NaHCO$_3$ and evaporation to dryness, the corresponding di-sodium salt is obtained, C$_6$H$_{12}$NO$_8$P.2Na, in crystalline form.

EXAMPLE 2

The same procedure of Example 1 is followed up to extraction of the lutidinium salt with CHCl$_3$. The evaporation residue of the CHCl$_3$ solution of said salt is dissolved into the minimum amount of methanol, and the obtained solution is applied on a column having a diameter of 2 cm containing about 30 ml of Amberlist 15(H$^+$), eluting with CH$_3$OH (∼200 ml); a solution of 1.2 g of NaHCO$_3$ in 30 ml of H$_2$O is added thereto, then the mixture is concentrated to a residual volume of about 45 ml, wherein the H$_2$O:CH$_3$OH volume ratio is 2:1. The solution is extracted several times with diisopropyl ether and then evaporated to small volume. The residue is dissolved in 80 ml of CH$_3$OH/H$_2$O (1:1 by volume) and hydrogenolyzed on 1.16 g of 10% palladium on charcoal. After filtration, the catalyst is washed with methanol/water 1:1 and the solution is evaporated to dryness under reduced pressure.

The obtained di-sodium salt obtained is dissolved in the minimum amount of water and transformed again into GPS acid by passing it on 55 ml of wet Amberlite IR-120(H$^+$) ® in a 3 cm diameter column, eluting with water.

The residue obtained by evaporation under reduced pressure of the aqueous eluate is kept under high vacuum on P$_2$O$_5$ up to constant weight, and to give pure GPS.

From the aqueous solution of the latter, by addition of the stoichiometric amount of K$_2$CO$_3$ and lyophilization, the di-potassium salt, C$_6$H$_{12}$NO$_8$P.2K, in crystalline form, is obtained.

EXAMPLE 3

The same procedures of Examples 1 and 2 are followed up to the isolation of GPS in the acid form.

By treatment of the aqueous solution with the stoichiometric amount of CaCO$_3$ and evaporation under vacuum, the mono-calcium salt, C$_6$H$_{12}$NO$_8$P.Ca, m.p. 175°–178° C., in crystal form, is obtained in substantially quantitative yields.

| Elemental analysis: for M.W. 297.216 | | | |
|---|---|---|---|
| calcd. % | C 24.23 | found % | C 24.15 |
| | H 4.07 | | H 4.13 |
| | N 4.71 | | N 4.69 |
| | P 10.42 | | P 10.38 |

NMR (80 MHz; D$_2$O: ppm 3.50–3.70 (m; 2H; CH$_2$ OH); 3.70–4.00 (m; 4H, CH$_2$ OP; 4.25–4.45 (m, 2H; CHOH; CHNH$_2$); 4.73 (s, 1H; DMO).

IR: 1670 cm$^{-1}$ (C=O); 1220 cm$^{-1}$ (P=O).

$[\alpha]_D^{20} = -8.25°$ (C=9.13 in H$_2$O).

EXAMPLE 4

The same procedures of Examples 2 and 3 are followed, but starting from D,L-α,β-isopropylidene glycerol. A calcium salt substantially identical to the previous one, but having $[\alpha]_D^{20} = -0.64°$ (C=12.28 in H$_2$O) is obtained.

The pharmacological experimentations on the effects of GPS on cerebral metabolism (1) and on neuronal transmission (2), are hereinafter reported in comparison with PS.

In the following tests, PS was dissolved in CHCl$_3$, evaporated under nitrogen stream, and after addition of Tris HCl, pH 7.4 50 mM, sonicated for 8 min. using a BROMSON sonicator. The GPS was dissolved in saline solution.

1. Effect on the cerebral glucose content

The influence of PS and GPS on cerebral metabolism was assessed by measuring the glucose in cerebral tissue according to the method described by Bigon (Brit. J. Pharmacol. 66, 167, 1979). The test was carried out on male albino mice treated by an intravenous route with 50 and 25 μmol/kg. Thirty seconds later, the animals were sacrificed, their brains removed, powdered with HClO$_4$ 0.66N and iced.

Weight was determined and, after centrifugation and neutralization, and glucose concentration was determined by an enzymatic method. The results obtained are reported in the following Table.

TABLE 1

Influence of PS and GPS on e cerebral glucose content.

| Treatment | Dose μmol/kg | N. animals | Cerebral glucose μmol/g wet weight |
|---|---|---|---|
| — | — | 45 | 2.05 = 0.06** |
| PS | 50 | 15 | 4.52 = 0.19 |
| PS | 25 | 15 | 2.38 = 0.10* |
| GPS | 50 | 15 | 4.72 = 0.17** |
| GPS | 25 | 15 | 2.49 = 0.15* | p vs. Controls
* $<0.05$
** $p <0.01$

2. Determination of 3',4'-cyclic AMP

Testing was carried out according to the method described by Albano (Anal. Biochem. 60, 130, 1974) by treating male rats, intravenously and killing the animals 20' later. The hypothalamic cyclic AMP was measured. The results are reported in the following Table.

TABLE 2

Effect of PS and GPS on the cAMP level in the rat hypothalamus.

| Treatment | Dose μmol/kg | N. rats | cAMP (pmol/mg protein) |
|---|---|---|---|
| — | — | — | 6.50 ± 0.46 |
| PS | 70 | 10 | 12.20 ± 0.97* |
| GPS | 70 | 10 | 13 ± 1.15* |

* p vs. Controls $<0.01$

3. Effect on dopamine turnover

The study was carried out on male rats treated with PS and GPS by oral and intraperitoneal routes. After 2 hours the animals were sacrificed and the 3,4-dihydroxyphenylacetic acid (DOPAC) concentrations were measured according to the method described by L. J. Felice et al. (J. Neurochem. 31, 1461, 1978). The obtained results are reported in the following Table.

TABLE 3

Effect of the oral and intraperitoneal administration of PS and GPS on the striatal concentrations of DOPAC.

| Treatment | Dose μmol/kg | N. animals | DOPAC ng/mg tissue os | DOPAC ng/mg tissue i.p. |
|---|---|---|---|---|
| — | — | 10 | 2.52 ± 0.27 | 2.60 ± 0.30 |
| PS | 10 | 10 | 2.63 ± 0.24 | 2.71 ± 0.27 |
| PS | 50 | 10 | 2.80 ± 0.18 | 2.83 ± 0.21 |
| PS | 100 | 10 | 3.11 ± 0.21 | 3.23 ± 0.18 |
| GPS | 10 | 10 | 2.48 ± 0.17 | 2.51 ± 0.28 |
| GPS | 50 | 10 | 2.65 ± 0.21 | 2.73 ± 0.20 |
| GPS | 100 | 10 | 2.93* ± 0.31 | 2.97 ± 0.18 |

* p vs. Controls $<0.01$

4. Effect on dopamine release

The evaluation of the dopamine release was carried out on slices of rat striatum removed two hours after the oral treatment with GPS and PS. The animals were previously treated with phenyl-ethyl-hydrazine (MAO-inhibitor).

The slices were pre-incubated with oxygenated Krebs-Ringer containing $^3$H-dopamine.

The radioactivity released in the medium during 10' was measured by means of a liquid phase scintillation spectrometer. The results are reported in the following Table.

TABLE 4

Effect of oral administration of PS and GPS on the dopamine release.

| Treatment | Dose μmol/kg | DA dpm/ng protein/10' |
|---|---|---|
| — | — | 3.541 ± 384 |
| PS | 10 | 4.121 ± 344 |
| PS | 50 | 7.844 ± 270* |
| GPS | 10 | 4.214 ± 302 |
| GPS | 50 | 8.015 ± 401* |

*p vs. Controls $<0.01$

5. Effect of GPS and PS on the ACh release

Testing was carried out on adult male rats orally treated with GPS and PS.

The ACh levels in the caudatum were evaluated by a radioenzymatic method (Brain Res. 87, 221, 1975).

TABLE 5

Effect of PS and GPS on the ACh levels in the rat caudatus nucleus.

| Treatment | Dose μmol/kg | N. rats | ACh nmol/g |
|---|---|---|---|
| — | — | 20 | 50.32 ± 5.3 |
| PS | 100 | 10 | 49.9 ± 7.2 |
| PS | 200 | 10 | 65.44 ± 1.4* |
| GPS | 100 | 10 | 53.64 ± 8.2 |
| GPS | 100 | 10 | 68.72 ± 6.3* |

*p vs. Controls $<0.05$

6. Metabolic fate of L-α-GP[3—$^{14}$C]L-serine

The study was carried out in mice treated with radioactive GPS administered by an intravenous route.

The $^{14}$C-labelled GPS was synthetized according to the method above described. Product purity was $\geq 96\%$, specific activity was 3 μCi/mg.

The mice were treated intravenously with 7 mg/kg (3 μCi/mg) of L-α-GP[3—$^{14}$C]L-Serine dissolved in saline solution.

The animals were sacrificed 5'/10'/20'/30' and 60' after treatment. Blood, liver and brain were removed and extracted according to the method of Folch et al. (J. Biol. Chem. 226, 497, 1957). The presence of GPS was detected in aqueous extracts.

The phospholipids, separated by chromatography, were removed from the plate and measured for radioactivity. The radioactivity connected with GPS was similarly measured.

The following phospholipids classes were identified in the blood and in the examined organs (liver and brain): lysophosphatidylserine, phosphatidylserine and phosphatidylethanolamine as well as GPS traces.

In the following Table, the mean values (relative to 5 animals) for each value are reported.

TABLE 6

Concentrations of different phospholipides and glycerophosphorylserine.

| Samples | PS | Lyso PS | PE | GPS |
|---|---|---|---|---|
| Blood nmol/ml | | | | |
| 5 | 120 ± 22.5 | 4 ± 0.75 | 3 ± 0.72 | 1 ± 0.84 |
| 10 | 92 ± 31.7 | 3 ± 0.92 | 3.2 ± 1.02 | — |
| 20 | 25 ± 9.6 | 1 ± 0.04 | 1.5 ± 0.09 | — |
| 30 | 7 ± 2.8 | — | — | — |
| 60 | 1.2 ± 0.9 | — | — | — |
| Liver nmol/g | | | | |
| 5 | 110 ± 42.7 | 5 ± 1.48 | 6 ± 1.24 | — |

TABLE 6-continued

Concentrations of different phospholipids and glycerophorylserine.

| Samples | PS | Lyso PS | PE | GPS |
|---|---|---|---|---|
| 10 | 147 ± 51.5 | 4.4 ± 1.95 | 5.8 ± 2.03 | — |
| 20 | 162 ± 42.7 | 2.9 ± 0.95 | 8 ± 2.12 | — |
| 30 | 154 ± 37.4 | 1.8 ± 0.75 | 9 ± 1.94 | — |
| 60 | 12 ± 3.4 | — | — | — |
| Brain nmol/g | | | | |
| 5 | 0.42 ± 0.03 | 0.03 ± 0.01 | 0.02 ± 0.001 | — |
| 10 | 1.65 ± 0.12 | 0.06 ± 0.009 | 0.08 ± 0.003 | — |
| 20 | 3.4 ± 0.23 | 0.05 ± 0.04 | 0.02 ± 0.002 | — |
| 30 | 2.7 ± 0.17 | 0.03 ± 0.001 | 0.01 ± 0.001 | — |
| 60 | 0.5 ± 0.04 | — | — | — |

As it is evident from the above Table, GPS is present only in the blood and only in the first 5 minutes after the administration and in barely detectable amounts.

Comparing these results with those reported in the literature (Phospholipids in the Nervous System—vol. I, Ed. L. Horrocks et al. Raven Press, N.Y. pag. 173, 1982), it can be affirmed that the GPS administered by the intravenous route follows the same metabolic fate of PS administered at equimolar doses.

It has been shown that in the animal test described hereinafter GPS is capable of counteracting cerebral insufficiency produced experimentally.

The test apparatus was a Skinner box (30×40×30 cm) with an electrifiable grid floor and a gray plastic platform (15×15×0.5 cm) in one corner. Naive male rats (100-120 g) were placed individually on the plastic platform. As soon as the animals moved off the platform a constant and continuous current of 0.8 mA was applied to the grid floor. The normal reaction of naive animals is to jump back onto the platform but because the test animals continued to step down, the shock procedure has to be repeated. After three to five trials (within 5 min.) the animals acquired a passive avoidance response, i.e. refrained from stepping down onto the grid floor.

Immediately after acquisition of the passive avoidance response, three groups (N=15) were of test animals formed. One group was injected with scopolamine HBr (1.0 mg/kg s.c.) and oral vehicle. The second group was injected with scopolamine HBr (1.0 mg/kg s.c.) and received a dose of the test substance by oral gavage.

The third group received the vehicle s.c. and orally.

Scopolamine and the test compound were dissolved in the vehicle (0.3% v/v Tween-80 in distilled water) and administered in a final volume of 2 ml/kg. Either 2 or 3 h after the passive avoidance training, each animal was placed once on the platform in the box to test retention of the acquired response. The criterion was whether the animal remained (yes) or did not remain (no) for at least 60 s on the platform.

A dose was considered to be active when the number of yes responses was significantly different from that in the vehicle-treated animals exposed to scopolamine HBr. The $x^2$ test was used for statistical analysis of the criterion significance of difference ($P<0.05$).

In the test described above, GPS was found to exhibit a significant activity after administration in doses of 0.3 mg/kg p.o., 3 mg/kg p.o. and 10 mg/kg.

Examples of pharmaceutical compositions suitable for oral administration include capsules, soft capsules, tablets, granulates, powders, solutions, lyophilized vials, sachets, and possible sustained-release forms, containing from 50 to 300 mg of GPSD (as such or as a salt with an alkali or alkali-earth metal, preferably as the calcium salt), per unit dose, to be administered 2-3 times a day according to the diagnosis and to the patient's conditions. For parenteral administration, both intravenous and intramuscular are suitable routes. Suitable forms for parental administration are lyophilized vials or sterile solutions containing 25-150 mg of glycerophosphoryl-O-serine (as such or as a salt with an alkali or alkali-earth metal, preferably as the calcium salt) to be administered from 1 to 3 times a day.

We claim:

1. A pharmaceutical composition for the therapy of cerebral involutive syndromes comprising:
   an effective involutive cerebral syndrome treating amount of an alkali or alkali-earth metal salt of glycerophosphoryl-O-serine and a pharmaceutically acceptable carrier therefor.

2. The pharmaceutical composition according to claim 1, which comprises glycerophosphoryl-O-serine calcium salt.

3. A pharmaceutical composition according to claim 1 which is suitable for oral administration.

4. A pharmaceutical composition according to claim 1 which is suitable for parenteral administration.

5. A pharmaceutical composition according to claim 1, which comprises an alkali or alkali-earth metal salt of 25 to 300 mg of glycerophosphoryl-O-serine per unit dose.

6. A pharmaceutical composition according to claim 5, which comprises glycerophosphoryl-O-serine calcium salt.

7. The pharmaceutical composition according to claim 1, which further comprises another drug having complementary or synergistic activity with said alkali metal or alkali-earth metal salt of glycerophosphoryl-O-serine.

8. A salt of glycerophosphoryl-O-serine with an alkali metal or an alkali-earth metal.

9. Glycerophosphoryl-O-serine calcium salt, of formula $C_6H_{12}NO_8PCa$.

10. A pharmaceutical composition according to claim 2, which is suitable for oral administration.

11. A pharmaceutical composition according to claim 2, which is suitable for parenteral administration.

12. The pharmaceutical composition according to claim 3, which comprises 25-300 mg of an alkali metal or alkali-earth metal salt of glycerophosphoryl-O-serine per unit dose.

13. The pharmaceutical composition according to claim 4, which comprises 25-300 mg of an alkali metal or alkali-earth metal salt of glycerophosphoryl-O-serine per unit dose.

14. A process for the preparation of the glycerophosphoryl-O-serine salts of claim 10 which process comprises:
   mixing an aqueous solution of glycerophosphoryl-O-serine with a stoichiometric amount of a hydroxide, a carbonate or a bicarbonate of an alkaline or an alkali-earth metal;
   and isolating said glycerophosphoryl-O-serine salt by evaporation or lyophilization from said solution.

15. A method of treating involutive cerebral syndromes, which method comprises administering to a mammal in need of such treatment an effective involutive cerebral syndrome treating amount of glycerophosphoryl-O-serine or an alkali metal or alkali-earth metal salt thereof.

16. A method of treating involutive cerebral syndromes, which method comprises administering to a mammal in need of such treatment an effective involutive cerebral syndrome treating amount of glycerophosphoryl-O-serine calcium salt.

17. A method of claim 15, wherein said glycerophosphoryl-O-serine or an alkali metal or alkali-earth metal salt thereof is administered intravenously, parenterally or intramuscularly.

18. The method of claim 15, wherein said involutive cerebral syndrome being treated is a vascular pathology of the atherosclerotic base.

19. The method of claim 15, wherein said involutive cerebral syndrome being treated is senile decay.

* * * * *